US010758260B2

(12) United States Patent
Roeder et al.

(10) Patent No.: US 10,758,260 B2
(45) Date of Patent: Sep. 1, 2020

(54) ULTRA-SONIC MEDICAL DISSECTOR AND METHOD OF DISEMBEDDING A MEDICAL DEVICE FROM SOFT TISSUE

(71) Applicant: Cook Medical Technologies LLC, Bloomington, IN (US)

(72) Inventors: Rebecca Roeder, Bloomington, IN (US); Joshua F. Krieger, Topsfield, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 471 days.

(21) Appl. No.: 15/598,419

(22) Filed: May 18, 2017

(65) Prior Publication Data

US 2018/0042635 A1    Feb. 15, 2018

Related U.S. Application Data

(60) Provisional application No. 62/373,614, filed on Aug. 11, 2016.

(51) Int. Cl.
| | | |
|---|---|---|
| *A61B 17/32* | (2006.01) | |
| *A61F 2/01* | (2006.01) | |
| *A61B 17/22* | (2006.01) | |

(52) U.S. Cl.
CPC ........ *A61B 17/320068* (2013.01); *A61F 2/01* (2013.01); *A61B 2017/22014* (2013.01);
(Continued)

(58) Field of Classification Search
CPC .............. A61B 17/22; A61B 17/22004; A61B 17/22012; A61B 17/2202; A61B 17/320068; A61B 17/320072; A61B 17/32056; A61B 17/50; A61B 2017/22005; A61B 2017/22007; A61B 2017/22008; A61B 2017/22009; A61B 2017/22011; A61B 2017/22014; A61B 2017/22015;
(Continued)

(56) References Cited

U.S. PATENT DOCUMENTS

| 4,854,325 A | 8/1989 | Stevens |
| 5,427,118 A | 6/1995 | Nita et al. |

(Continued)

FOREIGN PATENT DOCUMENTS

EP    2005912    12/2008

OTHER PUBLICATIONS

European Patent Office, European Search Report for Application No. 17183030.0, Published Jan. 8, 2018, Munich Germany.
(Continued)

*Primary Examiner* — Kathleen S Holwerda
*Assistant Examiner* — Kankindi Rwego
(74) *Attorney, Agent, or Firm* — Liell + McNeil

(57) ABSTRACT

An ultra-sonic medical dissector includes a vibration generator and a wire that defines a cutting loop remote from a first end and a second end. The wire is coupled to the vibration generator in a cutting configuration, and a cutting surface is located on an inner curvature of the cutting loop. A vibration is generated by the vibration generator is transmitted to the cutting loop by the wire when the wire is in tension. The cutting loop can free an embedded end of a vena cava filter from a vessel wall to ease retrieval.

12 Claims, 2 Drawing Sheets

(52) U.S. Cl.
CPC ......... *A61B 2017/320044* (2013.01); *A61B 2017/320072* (2013.01); *A61F 2/011* (2020.05); *A61F 2002/016* (2013.01)

(58) Field of Classification Search
CPC ......... A61B 2017/22017; A61B 2017/22018; A61B 2017/22035; A61B 18/14; A61B 2018/1402; A61B 2018/1405; A61B 2018/1407; A61B 2018/141; A61B 2018/1412; A61B 2018/1415; A61B 2018/1417; A61B 2018/142; A61B 2018/1422; A61F 2/01; A61F 2/95; A61F 2/954; A61F 2/2427; A61F 2002/011
See application file for complete search history.

(56) References Cited

U.S. PATENT DOCUMENTS

| | | | |
|---|---|---|---|
| 5,908,395 A | 6/1999 | Stalker et al. | |
| 6,231,578 B1 | 5/2001 | Rajhansa | |
| 6,383,194 B1 | 5/2002 | Pothula | |
| 6,514,267 B2 | 2/2003 | Jewett | |
| 6,869,439 B2 | 3/2005 | White et al. | |
| 9,301,828 B1 * | 4/2016 | Pursley | A61F 2/01 |
| 2006/0095046 A1 * | 5/2006 | Trieu | A61B 17/1671 |
| | | | 606/99 |
| 2008/0015409 A1 * | 1/2008 | Barlow | A61B 18/1492 |
| | | | 600/106 |
| 2012/0184987 A1 * | 7/2012 | Sirota | A61F 2/01 |
| | | | 606/200 |
| 2013/0150695 A1 | 6/2013 | Biela et al. | |
| 2014/0277087 A1 | 9/2014 | Manning | |

OTHER PUBLICATIONS

Ethicon US, LLC; Harmonic Synergy Blades, Published Jun. 5, 2015. Publisher: Ethicon US, LLC, Published in the United States.

* cited by examiner

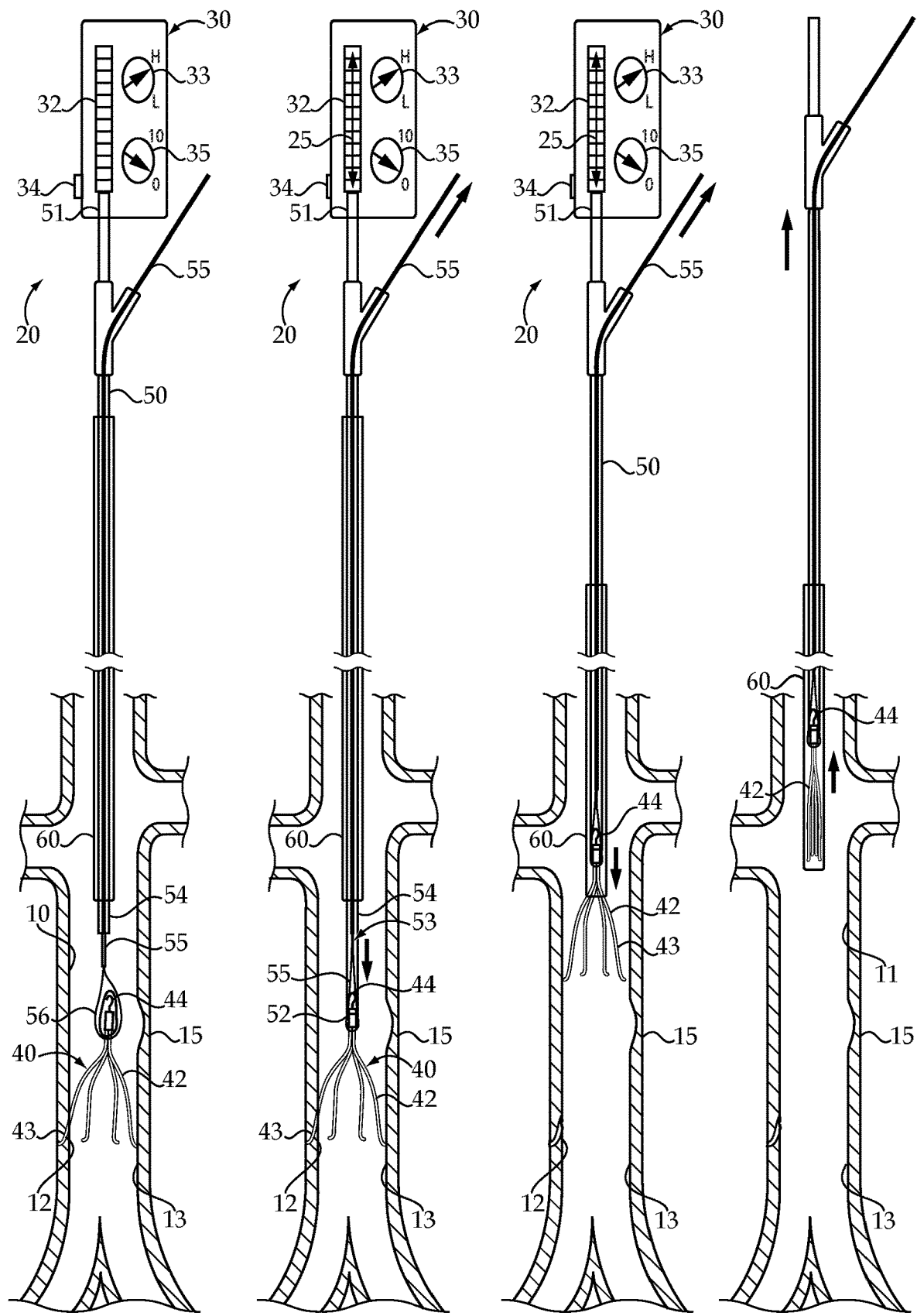

ULTRA-SONIC MEDICAL DISSECTOR AND METHOD OF DISEMBEDDING A MEDICAL DEVICE FROM SOFT TISSUE

TECHNICAL FIELD

The present disclosure relates generally to dissecting implanted medical devices from embedded soft tissue, and more particular to an ultrasonic medical dissector.

BACKGROUND

Retrieval of inferior vena cava (IVC) filters can be challenging, especially in cases where the filter has indwelt for long periods of time. The filter struts can embed in the wall of the IVC, or the filter tip can tilt and become embedded within the IVC wall. Once the filter has become embedded into soft tissue, retrieval becomes significantly more difficult and risky for the patient. Current retrieval methods often involve significant force or complex cutting, and are often high risk for the patient.

The present disclosure is directed toward one or more of the problems set forth above.

SUMMARY

In one aspect, an ultrasonic medical dissector includes a vibration generator and a wire that defines a cutting loop remote from a first end and a second end. The wire is coupled to the vibration generator in a cutting configuration. A cutting surface is located on an inner curvature of the cutting loop. A vibration generated by the vibration generator is transmitted to the cutting loop by the wire when the wire is in tension.

In another aspect, a method of disembedding a medical device that is embedded in soft tissue at a site includes a step of positioning a cutting loop of a wire in a space between the medical device and a vessel wall. The wire is coupled to a vibration generator remote from the cutting loop. The medical device is disembedded at least in part by vibrating the cutting loop with a vibration from the vibration generator while pulling a cutting surface on an inner curvature of the cutting loop through the soft tissue. The medical device is then moved away from the site.

BRIEF DESCRIPTION OF THE DRAWINGS

FIG. 5 is a schematic view of the medical device assembly in the early stages of a retrieval process;

FIG. 6 is a schematic view similar to FIG. 5 except later in the retrieval process according to one aspect of the present disclosure;

FIG. 7 is a schematic view of the medical device assembly after the implantable device has become disembedded;

FIG. 8 is a schematic view similar to FIGS. 1-3 showing the implantable device being moved away from the embedding site.

DETAILED DESCRIPTION

Figures 1, 2, 3, 4:
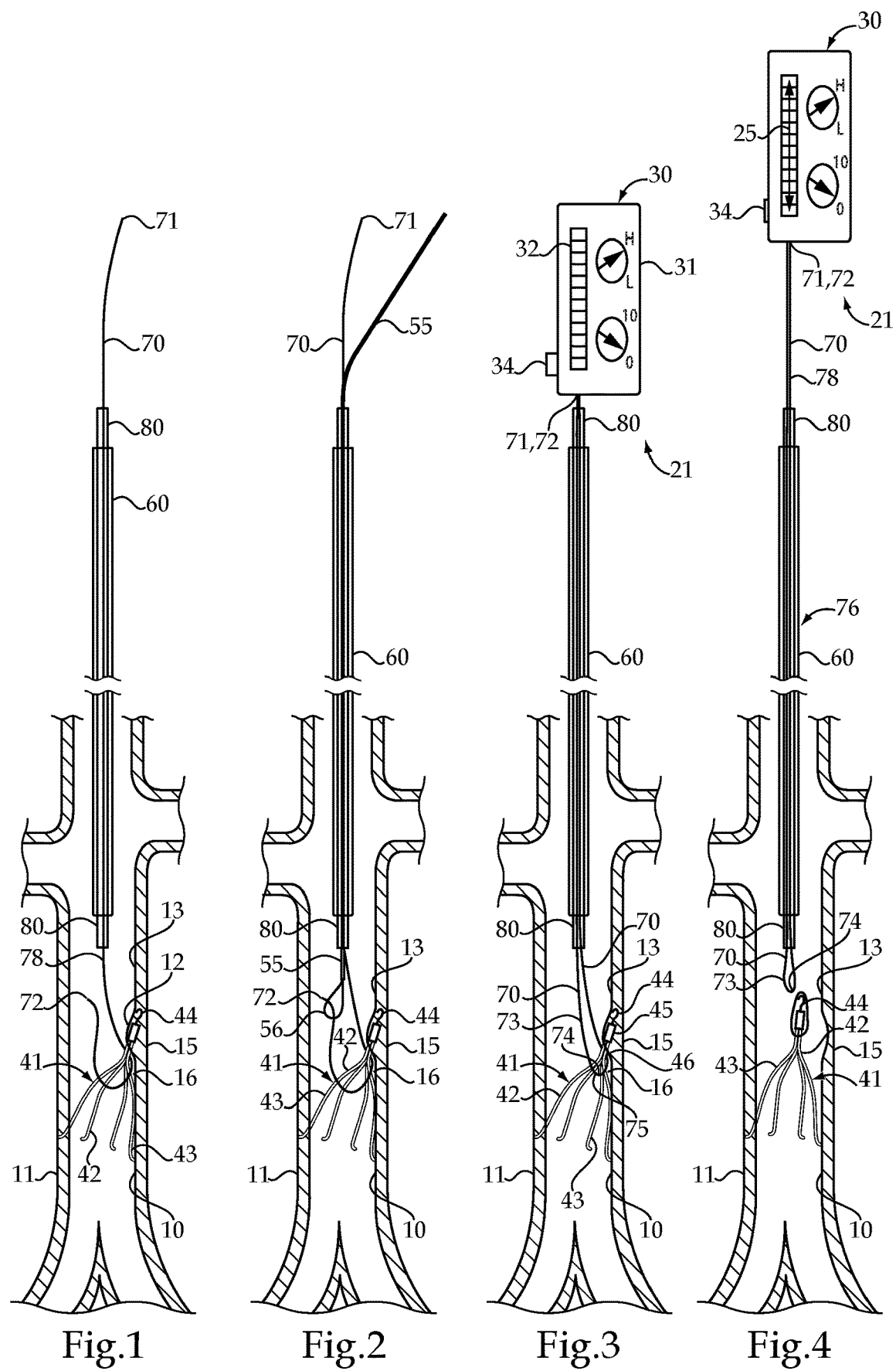
FIG. 1 is a schematic view of a medical device disembedding procedure in the early stages of the process.
FIG. 2 is a schematic view similar to FIG. 1 except later in the disembedding process.
FIG. 3 is a schematic view similar to that of FIGS. 1 and 2 also showing an ultrasonic medical dissector according to the present disclosure.
FIG. 4 is a schematic view similar to FIGS. 1-3 after the ultrasonic medical dissector has disembedded a capture end of a vena cava filter according to one aspect of the present disclosure.

Referring initially to FIGS. 1-4, a strategy for disembedding a blood filter 42 whose capture end 44 has become embedded in soft tissue 12 is illustrated. In some instances, an inferior vena cava filter 42 can become tilted in a blood vessel 10, which is shown as the inferior vena cava 11, such that the captured end 44 becomes embedded in soft tissue 12. The present disclosure teaches a new strategy for dissecting the capture end 44 out of the soft tissue 12 so that the filter 42 may be retrieved or moved in a conventional manner. The process begins at FIG. 1 where a wire 70 is slid through a catheter 80, which may be received in a sheath 60. An end 72 of wire 70 is passed through the space 16 that is defined between filter 41 and the wall 13 of blood vessel 10. Thereafter, as shown in FIG. 2, a snare 55 may be used to capture end 72 with a loop 56 of snare 55. Thereafter, the end 72 is pulled back up through catheter 80 utilizing snare 55 so that both ends 71 and 72 are located out of the proximal end of catheter 80 leaving a cutting loop 73 looped through space 16 as shown in FIG. 3. When in the configuration shown in FIG. 3, an ultrasonic medical dissector 21 can be assembled using a vibration generator 30 and wire 70. The wire 70 defines a cutting loop 73 that is remote from a first end 71 and a second end 72. The wire 70 is coupled to the vibration generator 30 in a cutting configuration as shown in FIG. 3. The wire 70 includes a cutting surface 74 that is located on an inner curvature 75 of the cutting loop 73. At least one of the ends 71 and 72 of wire 70 are connected to the vibration generator 30. Vibration generator 30 may include a piezo stack 32 housed in a handle 31 that includes an activation switch 34. When the vibration generator 30 is turned on, an ultra-sonic vibration generated may be transmitted to the cutting loop 73 by the wire 70 when the wire 70 is in tension. Thus, as shown in FIG. 4, when the vibration generator 30 is turned on to produce a vibration 25, the wire 70 may be placed in tension so that the cutting loop 73 slides along, and may be guided by, an outer surface 46 to cut the end 44 out of the soft tissue 12 in which it has become embedded. Thus, the ultrasonic medical dissector 21 may utilize the outer surface 46 of the filter 41 as a cutting guide 45 when the cutting loop 73 is maneuvered to liberate the end 44.

The ultrasonic medical dissector 21 may include a catheter 80 that is positioned between the vibration generator 30 and the cutting loop 73. At least one segment 78 of the wire adjacent the cutting loop 73 is received in the catheter 80. FIG. 3 shows the ultrasonic medical dissector in a cutting configuration. The ultrasonic medical dissector 21 may also have a pre-cutting configuration in which at least one segment of the wire 70 is de-coupled from the vibration generator 30.

After the end 44 of filter 42 has been freed from the vessel wall 13 as shown in FIG. 4, the inferior vena cava filter 42 may be retrieved using known techniques, such as a snare that captures end 44 along with a sheath for receiving the captured blood filter 42. However, FIGS. 1-4 show a circumstance in which both the tilted end 44 of the blood filter 42 has become embedded in soft tissue 12 but also one of the legs 43 has become embedded in the vessel wall. According to the present disclosure, after the end 44 has been cut free of the vessel wall 13 as shown in FIG. 4, a different technique using a vibration generator 30 may be utilized to complete the liberation of filter 42 by disembedding the leg 43 from the vessel wall 13 as discussed infra.

Referring now to FIGS. 5-8, a medical device assembly 20 includes a vibration generator 30, which may be suitable for generating ultrasonic vibrations in a manner known in the art. This aspect of the disclosure is apt when one or more of the legs 43 of the filter 42 are also embedded in soft tissue, after the capture end 44 has been cut free. As discussed earlier, vibration generator 30 includes a piezo stack actuator 32 positioned in a handle 31. Vibration generator 30 may also include an activation switch 34, a vibration frequency controller 33 and maybe a vibration magnitude controller 35. In the illustrated embodiment, vibration generator 30 used with medical device assembly 20 is shown identical to the vibration generator 30 used as part of the ultrasonic medical dissector 21 of FIGS. 1-4. Nevertheless, the vibration generators 30 for the ultrasonic medical dissector 21 (FIGS. 1-4) and the medical device assembly 20 (FIGS. 5-8) could be completely different devices without departing from the intended scope of the present disclosure. Medical device assembly 20 also includes an implantable device 40 that is shaped for temporary or permanent implantation in a blood vessel 10. In the illustrated embodiment, implantable device 40 takes the form of an inferior vena cava filter 42. Nevertheless, implantable device 40 could be another type of filter, a stent, graft or maybe even a pacemaker lead, or any other known implantable device that is shaped for temporary or permanent implantation in a blood vessel without departing from the present disclosure. Medical device assembly 20 also includes a vibration transmission apparatus 50 with one end 51 coupled to the vibration generator 30, and an opposite end 52 in contact with the implantable device 40 (FIG. 6). The medical device assembly 20 can be utilized to assist in disembedding the implanted device 40 from soft tissue by causing features of the implanted device (e.g. filter legs 43) to vibrate and act locally like an ultrasonic knife to assist in vibrating the implanted device 40 out of the soft tissue in which it is embedded. As used in this disclosure, "coupling" can be as simple as contact or as complex as a simultaneous push/pull connection facilitated by a snare 55 and cannula 54.

In the illustrated embodiment, the vibration transmission apparatus 50 includes a cannula 54 and a tension member 53, which may take the form of a snare 55 with a loop 56 snared to the end 44 of the inferior vena cava filter 42. In the illustrated embodiment, at least one leg 43 of the inferior vena cava filter 42 has become embedded in soft tissue 12 in the wall 13 of the inferior vena cava 11. After snaring end 44, the cannula 54 may be advanced into contact with the inferior vena cava filter 42 as shown in FIG. 6. While maintaining some tension via the snare 55, the vibration generator 30 may be turned on as shown in FIG. 7. When this occurs, leg(s) 43 of the inferior vena cava filter 42 will vibrate responsive to a vibration transmitted from the vibration generator 30 to the filter 42. As a result, the filter may rapidly free itself, or at least become freed with a reduced pulling force, from being embedded in the soft tissue of the blood vessel 10, and permit a conventional retrieval sheath 60 to be advanced over the filter 42 and allow the same to be removed from the patient's body as shown in FIG. 8.

Although not necessary, the vibration 25 may include a predetermined frequency that is correlated to a frequency response property of the implantable device 40 or the tissue, or both. In some instances, it may be advantageous to utilize a vibration frequency that can excite one or more natural frequencies of the implantable device 40. Furthermore, lab testing could allow for identification of certain frequencies that may be best suited for individual known implanted devices. For instance, one frequency may work well for a Tulip type filter, whereas another frequency may perform better for a Celect™ or a Greenfield™ filter. Accordingly, the vibration frequency controller 33 may be marked with different filter types instead of with numerical frequency selections without departing from the scope of the present disclosure. In such a way, the physician need only determine the type of filter implanted in the patient and then adjust the vibration generator to the frequency best suited for disembedding that particular filter type.

INDUSTRIAL APPLICABILITY

The present disclosure finds general applicability to disembedding, and possibly retrieving, implantable medical devices from a patient. The present disclosure finds specific applicability to disembedding and retrieving embedded inferior vena cava filters. The present disclosure also finds specific applicability to disembedding blood filters that are tilted so that the capture end has become embedded in the soft tissue of the vessel wall.

Referring again to FIGS. 1-4, a method of disembedding a medical device such as a blood filter that is embedded in soft tissue at a site 15 is illustrated. The process begins by threading a first end 72 of a wire 70 through a space 16 that has a closed perimeter defined by the vessel wall 13 and the embedded medical device, which is a vena cava filter 42 in the illustrations. This portion of the procedure is shown in FIG. 1. Next, the end 72 of wire 70 may be snared with a snare 55 shown in FIG. 2. The snare 55 may then be used to move end 72 of wire 70 toward the vibration generator 30. This results in a cutting loop 73 being trapped in the space 16 as best shown in FIG. 3. Thus, the portion of the process shown in FIGS. 1 and 2 effectively positions cutting loop 73 of wire 70 in the space 16 between the blood filter 42 and the vessel wall 13.

The wire 70 may be coupled to the vibration generator 30 by connecting a segment, which terminates at one of the first end 71 and the second end 72, to the handle 31 of vibration generator 30. Alternatively, only one end 71 or 72 of wire need be coupled with vibration generator 30 provided that the opposite end of the wire is held in a fixed position so that movement of vibration generator 30 can apply tension to the wire 70 in general, and the cutting loop 73 in particular. After the ultrasonic medical dissector 21 is configured as shown in FIG. 3, the vibration generator 30 may be turned on while applying tension to wire 70. This tension will facilitate transmitting the vibration 25 from the piezo stack 32 along wire 70 to the cutting loop 73. The blood filter 42 may then be dissected from the soft tissue 12 at least in part by vibrating the cutting loop 73 with the vibration 25 from the vibration generator 30 while pulling a cutting surface 74 on a inner curvature 75 of the cutting loop 73 through the soft tissue 12. This cutting procedure may be guided by movement of the cutting loop 73 through the soft tissue 12 while being guided on an outer surface 46 of blood filter 42. After the end 44 of blood filter 42 has been cut free from vessel wall 13, the ultrasonic medical dissector 21 may be withdrawn from sheath 60. If no other portion, such as a leg 43, is embedded in the vessel wall 13, the now free blood filter 42 may be retrieved in a conventional manner using a snare 55 and a retrieval sheath 60. However, in the illustrated embodiment, even after the end 44 has been cut free of the vessel wall 13, a leg 43 of the blood filter 43 is shown as itself being embedded in the vessel wall 13. In such a case, another vibration strategy may be utilized to liberate the leg 43 from the vessel wall 13 to facilitate retrieval in a conventional manner using a snare 55 and a retrieval sheath 60.

Referring again to FIGS. 5-8, a method of retrieving an implanted device 40 (filter 42) that is partially embedded in soft tissue 12 at a site 15 includes coupling a vibration transmission apparatus 50 to the implanted device 40. In the illustrated embodiment, in the case of a embedded inferior vena cava filter 42, the process may begin by grasping the now free end 44 of the filter 42 with a loop 56 of a snare 55. Next, a cannula 54 is slid along the snare 55 into contact with filter 42 as shown in FIGS. 2 and 3. The filter 42 is then disembedded from the soft tissue 12 at least in part by generating a vibration 25 with the vibration generator 30 while gently pulling on the snare 55. The vibration 25 is transmitted along the vibration transmission apparatus 54, 55 to the filter 42 to cause the implanted device 40 to vibrate. This may be accomplished after cannula 54 has been advanced into contact with the filter 42. A snare 55 may be placed in tension while the vibration is transmitted so that when the filter 42 begins to vibrate there is a slight pulling force to help withdraw the same from the soft tissue 12. After becoming disembedded, the implanted device 40 may be moved away from the site 15, such as by pulling the filter 42 from outside of a sheath 60 into the sheath 60 for removal from the patient's body. In the illustrated embodiment, the cannula 54 is in contact with, but not attached to, the distal end 44 of the inferior vena cava filter 42. The distal end of the cannula 54 may be in contact with one or more of the legs 43 of the filter 42. Cannula 54 should be sufficiently rigid that a vibration generated by vibration generator 30 can successfully be transmitted without becoming overly damped before arriving at the filter 42 that is embedded in the soft tissue 12. In the illustrated embodiment, the end of the filter 42 may actually be received into the cannula 44 when the vibration 25 is transmitted. In some instances, it may be useful to change at least one of a vibration's magnitude and a vibration frequency in order to successfully disembed the implanted device from the surrounding soft tissue 12.

Current vena cava filter retrieval methods can involve significant force or complex cutting, and are high risk for a patient. The present disclosure provides a method of filter retrieval that can minimize tissue damage and reduce patient risk, while also providing a significantly faster procedure than current retrieval methods, and with considerably less pulling force.

The present description is for illustrative purposes only, and should not be construed to narrow the breadth of the present disclosure in any way. For instance, although the method(s) is disclosed in the context of a live body, the disclosed method(s) could also be performed on artificial tissue to demonstrate the technique without a live body, such as for teaching purposes. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. An ultrasonic medical dissector comprising:
    a vibration generator;
    a wire defining a cutting loop, and including a first end and a second end, and the wire being coupled to the vibration generator in a cutting configuration, and a cutting surface of a cutting loop being located on an inner curvature of the cutting loop, and the cutting loop being a greater distance from the vibration generator than a respective distance of each of the first end and the second end are to the vibration generator in the cutting configuration;
    a snare with a loop;
    wherein a vibration generated by the vibration generator is transmitted to the cutting loop by the wire when the wire is in tension;
    wherein the wire and the vibration generator have a pre-cutting configuration characterized by the first end of the wire being remote and decoupled from the vibration generator and captured by the loop of the snare for pulling the first end of the wire toward, to be coupled with, the vibration generator in the cutting configuration;
    a cutting guide that is located adjacent the cutting loop; and
    wherein the cutting guide is an outer surface of a blood filter.

2. The ultrasonic medical dissector of claim 1 including a catheter positioned between the vibration generator and the cutting loop;
    at least one segment of the wire adjacent the cutting loop is received in the catheter.

3. The ultrasonic medical dissector of claim 1 wherein the blood filter is an inferior vena cava filter.

4. The ultrasonic medical dissector of claim 1 wherein the vibration generator includes a piezo stack positioned in a handle.

5. The ultrasonic medical dissector of claim 4 including a catheter positioned between the vibration generator and the cutting loop;
    at least one segment of the wire adjacent the cutting loop is received in the catheter.

6. A method of disembedding a medical device that is embedded in soft tissue at a site, comprising the steps of:
    positioning a cutting loop of a wire in a space of an enclosed perimeter defined by the vessel wall and the medical device;
    coupling the wire to a vibration generator remote from the cutting loop;
    disembedding the medical device at least in part by vibrating the cutting loop with a vibration from the vibration generator while pulling a cutting surface on an inner curvature of the cutting loop through the soft tissue;
    moving the medical device away from the site;
    wherein the positioning step includes threading a first end of the wire through the space;
    wherein the positioning step includes snaring the first end of the wire with a loop of a snare; and
    moving the first end of the wire toward the vibration generator with the snare.

7. The method of claim 6 wherein the coupling step includes connecting a segment of the wire that terminates at the first end to a handle of the vibration generator.

8. The method of claim 6 wherein the disembedding step includes tensioning the wire; and
    transmitting the vibration from the vibration generator to the cutting loop through the tensioned wire.

9. The method of claim 6 wherein the disembedding step includes guiding movement of the cutting loop through the soft tissue with an outer surface of the medical device.

10. The method of claim 9 wherein the medical device is a blood filter; and
    the outer surface includes an outer surface of a leg of the blood filter.

11. The method of claim 10 wherein the disembedding step includes tensioning the wire; and
transmitting the vibration from the vibration generator to the cutting loop through the tensioned wire.

12. The method of claim 11 wherein the moving step includes moving at least a portion of the blood filter into a retrieval sheath.

\* \* \* \* \*